United States Patent
Taff et al.

(10) Patent No.: US 9,493,261 B2
(45) Date of Patent: Nov. 15, 2016

(54) STERILIZABLE CONTAINMENT FOR IMPLANTABLE MEDICAL DEVICE

(71) Applicant: BIOTRONIK SE & CO. KG, Berlin (DE)

(72) Inventors: Brian M. Taff, Portland, OR (US); Hannes Kraetschmer, West Linn, OR (US); Jeffrey A. von Arx, Lake Oswego, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 151 days.

(21) Appl. No.: 14/543,646

(22) Filed: Nov. 17, 2014

(65) Prior Publication Data
US 2015/0142073 A1    May 21, 2015

Related U.S. Application Data

(60) Provisional application No. 61/906,902, filed on Nov. 21, 2013, provisional application No. 61/992,930, filed on May 14, 2014.

(51) Int. Cl.
| | |
|---|---|
| *A61L 2/00* | (2006.01) |
| *B65B 55/02* | (2006.01) |
| *A61N 1/362* | (2006.01) |
| *A61N 1/372* | (2006.01) |
| *A61N 1/375* | (2006.01) |

(52) U.S. Cl.
CPC .............. *B65B 55/02* (2013.01); *A61B 50/00* (2016.02); *A61N 1/362* (2013.01); *A61N 1/3756* (2013.01); *A61N 1/3758* (2013.01); *A61N 1/37217* (2013.01); *A61N 2001/37294* (2013.01)

(58) Field of Classification Search
CPC ................................ B65B 55/02; A61N 1/362
USPC .............................. 607/36; 206/570; 422/22
See application file for complete search history.

(56) References Cited

U.S. PATENT DOCUMENTS

| | | |
|---|---|---|
| 4,423,732 A | 1/1984 | Tarjan et al. |
| 4,588,085 A | 5/1986 | Sussman |
| 4,605,007 A | 8/1986 | Heraly |
| (Continued) | | |

FOREIGN PATENT DOCUMENTS

FR    2483215 A3    12/1981

OTHER PUBLICATIONS

European Search Report received in EP Application Serial No. 14189466, dated Mar. 5, 2015, 8 pages.

*Primary Examiner* — Kevin Joyner
(74) *Attorney, Agent, or Firm* — ARC IP Law, PC; Joseph J. Mayo

(57) ABSTRACT

A sterilizable containment that includes an inner packaging and an outer packaging. The outer packaging encloses the inner packaging and includes at least two electric feedthroughs. The inner packaging includes at least two electric contacts, wherein each of the at least two electric contacts of the inner packaging matches one of the at least two electric feedthroughs of the outer packaging to provide an electric connection between a respective feedthrough and the corresponding contact when the inner and the outer packaging are closed. Each of the contacts of the inner packaging feed electrical charge from outside of the inner packaging to the inside of the inner packaging and vice versa. The inner packaging includes electrically conducting media that allows propagation of electrical charge between the contacts of the inner packaging and an implantable medical device included inside in a packaging when the containment is filled.

15 Claims, 6 Drawing Sheets

(56) References Cited

U.S. PATENT DOCUMENTS

| | | |
|---|---|---|
| 6,116,413 A | 9/2000 | Tabor et al. |
| 6,181,105 B1 | 1/2001 | Cutolo et al. |
| 6,292,697 B1 | 9/2001 | Roberts |
| 2002/0161402 A1 | 10/2002 | Vogel et al. |
| 2006/0020300 A1 | 1/2006 | Nghiem et al. |
| 2007/0123947 A1 | 5/2007 | Wenger et al. |
| 2009/0124965 A1 | 5/2009 | Greenberg et al. |
| 2010/0004639 A1 | 1/2010 | Pang et al. |
| 2010/0114247 A1 | 5/2010 | Snitting |

STERILIZABLE CONTAINMENT FOR IMPLANTABLE MEDICAL DEVICE

This application claims the benefit of U.S. Provisional Patent Application 61/906,902 filed on 21 Nov. 2013, and U.S. Provisional Patent Application 61/992,930 filed on 14 May 2014, the specifications of which are hereby incorporated herein by reference.

BACKGROUND OF THE INVENTION

1. Field of the Invention

Embodiments of the invention generally relate to a sterilizable containment for an implantable medical device or containing an implantable medical device. Embodiments of the implantable medical device may include an implantable programmable heart stimulator, such as an implantable pacemaker or an implantable cardioverter/defibrillator. Embodiments of the invention also generally relate to a method of communicating with an implantable medical device while placed in the sterilizable containment.

2. Description of the Related Art

Generally, implantable medical devices are sterilized prior to use. Therefore, a containment is typically needed, wherein the implantable medical device may be maintained in a sterilized state. To ensure that the implantable medical device remains sterile, the implantable medical device is generally sterilized together with a containment enclosing the device.

Examples of implantable medical devices include implantable leadless pacemakers (ILP) that are small enough to be placed within a ventricle of a human heart. Such implantable leadless pacemakers typically feature two electrodes that are arranged on the pacemaker's casing and that may deliver stimulation pulses to a medium or tissue surrounding the implantable leadless pacemaker when in use. Traditional pacemakers are implanted distal to the heart and connected to separately implanted electrode leads with electrodes for sensing and stimulation within the heart. For implantable leadless pacemakers, generally no electrode leads are needed and therefore only one device needs to be implanted and kept sterile prior to implantation.

Implantable medical devices generally include a communication unit to communicate with an external device such as a programmer for programming of the device and interrogation of device data. Traditional pacemakers often use wireless communication with radio frequencies or by magnetic coupling by coils. Such communication techniques typically require a significant amount of energy for transmission and size for antennas or communication coils that may be not available in small implantable medical devices such as implantable leadless pacemaker (ILP). Alternative communication techniques more suitable, for example, for implantable leadless pacemaker (ILP) are generally based on a galvanic or electrical conductive coupling between the implantable medical device and the external device. In general, galvanic communication is referred to as communication that is based on alterations of electric charges, either by altering capacitive coupled small electric fields or by altering a current of voltage via a galvanic connection between transmitter and receiver. This typically requires an electrical conductivity or capacitive coupling between the programmer and the implantable medical device. In an implanted state, the body generally provides such an electrical conductivity or capacitive coupling between electrodes of the implanted medical device and tissue surface electrodes connected to the external device.

A further alternative communication technique more suitable, for example, for implantable leadless pacemaker (ILP) is generally based on a small electric field imposed on the implantable medical device. Data is typically transmitted to the implantable medical device by modulating the electric field. The implantable medical device on the other hand generally transmit data by altering the imposed electric field, e.g. by generating an electric field between the device electrodes. This typically requires only a capacitive coupling of electrodes connected to the external device to the implantable medical device.

Another method of communication, referred to as active galvanic communication, is generally based on the transmission of voltage or current pulses by electrodes of the transmitting device that are galvanically conducted by the body to electrodes of the receiving device. In both cases, galvanic or electrical conductive paths between the implantable medical device and the external device are typically required.

Generally, there is no available solution for enabling galvanic communication with an implant in a manner that avoids breaching of its sterile packaging or runs acute risk for contaminating the sterility of the implantable medical device prior to installation within the patient receiving therapy. Communication between the implantable medical device and the programmer, when the implantable medical device is stationed outside of the cardiac volume, typically leverages either placement of the implantable medical device into a conductive water bath with appropriate electrical connections or direct electro-mechanical interfacing with the implant's electrodes.

Alternative Solutions and Drawbacks

Generally, known systems require data exchange with the implant that is performed using special equipment prior to device sterilization and packaging procedures; or performed within a sterile field, using special equipment that unnecessarily crowds the clinical environment and adds risk of contamination; or performed subsequent to routing the implantable medical device through the patient's vasculature and into the cardio vascular volume or in general into the body where it may relay data to skin-mounted conductive pads. In cases where an implantable medical device is either permanently contaminated or damaged as a result of alternative strategies for communication support, it is typically necessary to scrap the implantable medical device and unpack another replacement implantable medical device to provide leadless therapy. Furthermore, contamination generally cannot be easily detected during an implant procedure, as such it may likely lead to an infection. Such waste typically demands accommodation for yield loss and customer support management that is generally highly political and unnecessarily challenging.

Generally, placing the implantable medical device within a dedicated conductive saline bath requires assurances that either the saline bath is sterile (if the implant is to be implanted following such treatments); or additional procedures are run to re-sterilize the implantable medical device prior to its use in delivering patient therapies. To maintain a sterile saline bath generally means that precious real estate within the clinical sterile field is unfortunately consumed. Conversely, added sterilization steps after opening a sterile implantable medical device typically present the potential for increasing patient infection risks, extending the duration of implant procedures, risk of damaging the device if improper sterilization parameters are used, and again demanding the placement of special equipment within the sterile field to return the implant to an implantable condition.

Typically, such procedures may even nullify the intent of sterile packaging. Re-sterilization is contra-indicated in most active implantable medical device labeling. Employing direct electro-mechanical interfacing with the implantable medical device's electrodes also typically runs the risk for implantable medical device contamination (via excess handling) and furthermore generally presents an increased potential for damaging the implantable medical device's electrodes. The implantable medical device's electrodes are typically covered with fractal coatings and carefully-defined exposed active areas. Mechanical abrasions associated with deliberate electro-mechanical contact may generally undesirably alter their capabilities for pacing, sensing, and supporting galvanic communication.

In view of the above, inventors have recognized the need for packaging for implantable medical devices in a sterile containment that enables galvanic data exchange with a programmer while the containment is sealed.

In addition, in view of the above, there is a need to enable galvanic or electrical conductive paths that support the activation, programming, and interrogation of implantable medical devices after sterilization and packaging procedures have been completed. In addition, there is a need to enable developer support for non-invasive/non-destructive device debug/testing.

Furthermore, in view of the above, there is a need to enable an electrical conductive or capacitive coupling to the implantable medical device to program the implantable medical device prior to the implantation when the device is in a sterile containment.

BRIEF SUMMARY OF THE INVENTION

One or more embodiments of the invention provide a suitable containment for an implantable medical device, and in particular for a programmable implantable leadless pacemaker.

At least one embodiment of the invention includes a sterilizable containment that includes an inner packaging and an outer packaging. In one or more embodiments, the outer packaging encloses the inner packaging and includes at least two electric feedthroughs. In at least one embodiment, the inner packaging may include at least two electric contacts, wherein each of the contacts of the inner packaging matches one of the feedthroughs of the outer packaging to provide an electric connection between a respective feedthrough and the corresponding contact when the inner and the outer packaging are closed. In at least one embodiment, the containment and the inner and the outer packaging may be opened prior to insertion of an implantable medical device into the containment. In one or more embodiments, the implantable medical device may be placed in the inner packaging, and then the inner and the outer packaging are closed. Afterwards, in at least one embodiment, the sterilizable containment with the implantable medical device may be sterilized. In one or more embodiments, reopening of the containment in order to remove the sterile implantable medical device may occur immediately prior to implantation.

By way of at least one embodiment, each of the contacts of the inner packaging may be configured and arranged to provide electrical conductivity or capacitive coupling from outside of the inner packaging to the inside of the inner packaging. In one or more embodiments, the inner packaging may include electrically conducting media that provides electrical conductivity or capacitive coupling between the contacts of the inner packaging and an implantable medical device contained inside in a packaging when the containment is filled.

In at least one embodiment, the electric feedthroughs of the outer packaging and the electric contacts of the inner packaging may allow delivery of an electrical charge to the medium inside the inner packaging and may measure the impedance or a electric field between the contacts of the inner packaging, which depends on the medium contained in the inner packaging that is influenced by the implantable medical device. Thus, one or more embodiments of the invention may communicate galvanically with an implantable medical device even when the implantable medical device is contained in the containment and the inner and the outer packaging are closed. As such, in at least one embodiment, communication with the implantable medical device may occur without opening the inner and the outer packaging, such that the implantable medical device may be kept sterile while, for instance, programming the implantable medical device.

The inventors have recognized that there is a need for novel packaging, module, and/or programmer considerations to enable such flexibilities to enable galvanic programming (and/or activation) of the device within the sterile package. One or more embodiments of the invention may include metal connections (such as foil or electrode pins) that pass through the packaging and interface with the device. In at least one embodiment, the interfacing with the device may involve direct connections, capacitive coupling, or even impedance-based strategies. One or more embodiments of the invention may include a cavity filled with a conductive fluid or gel that may house the device and provide an electrical connection to a packaged medical implant; as shown in the figures and discussed further below. In at least one embodiment, a programmer may then connect to the feedthroughs metal tabs on the outer surface of the outer packaging and because of the electrical connection to the device, activation and programming of the implant may occur galvanically without having to remove the implant from a sterile containment.

One or more embodiments of the invention facilitate galvanic communication with an implantable medical device, such as an ILP, prior to implantation while maintaining the implantable medical device within sterile packaging. In at least one embodiment, implantable leadless pacemakers may employ an impedance-based technique to enable communication between the implant and the programmer. According to one or more embodiments, this strategy, referred to as passive galvanic communication, utilizes a dynamically-controlled switch (located within the implantable medical device) to modify the implantable leadless pacemaker's electrode impedance. In at least one embodiment of the invention, the modification of the electrode impedance may be modulated by the implantable medical device and detected by either distally-stationed receiver electrodes (typically ECG pads or skin surface electrodes) or via direct contact with the implantable medical device. In one or more embodiments, the principle may be also used for the opposite communication direction, wherein a modulated impedance between the electrodes of the external device may be detected by the implantable medical device.

With respect to active galvanic communication, embodiments of the invention enable the activation, programming, and interrogation of implantable medical devices after sterilization and packaging procedures have been completed.

Embodiments of the invention additionally enable developer support for non-invasive/non-destructive device debug/testing According to at least one embodiment of the invention, the implantable medical device may allow a galvanic communication. In one or more embodiments, the implantable medical device t may communicate galvanically wherein the implantable medical device may influence a small electric field that is imposed on the medium surrounding the implantable medical device. In at least one embodiment, passive galvanic communication may be achieved by providing an implantable medical device that alternatingly establishes and disconnects a connection between two electrode poles of the implantable medical device to thus alter the impedance between the two electrodes and the impedance of the medium containing the implantable medical device. In one or more embodiments, the implantable medical device may generate a small local electric field that is detectable or influences an imposed electric field.

In at least one embodiment, the electric conducting medium contained in the inner packaging may include a fluid or a liquid gel, such as saline or a conductive gel. In one or more embodiments, the conductive medium may be a conductive solid material, such as a conductive foam or for example steel wool. In at least one embodiment, the conductive medium may include a solid material, wherein the solid material may be arranged within the inner packaging to conduct electric current or to allow propagation of an electric field between the contacts of the inner packaging and the electrode poles of the implantable medical device within the inner packaging.

In at least one embodiment, the outer packaging may include four feedthroughs, and the inner packaging may include four contacts. As such, in one or more embodiments, using two feedthroughs together with two contacts may impose an electric field on the medium in the inner packaging. The other two feedthroughs and the corresponding contacts, in at least one embodiment, may be used to measure signal response for current or voltage or impedance or electric field measurement, respectively. The resulting 4-point measurement, in one or more embodiments, instead of using two feedthroughs, eliminates the signal loss through the packaging from the measured signal.

In at least one embodiment, the contacts of the inner packaging may include inner feedthroughs that may feed connections from outside of the inner packaging to the electrically conducting medium inside the inner packaging. As such, in one or more embodiments, the contacts may be part of a conductor that terminates inside the inner packaging. In at least one embodiment, the contacts and the feedthrough provided by the contacts of the inner packaging may be configured to allow a capacitive coupling between the contact and the electrically conducting medium inside the inner packaging.

According to one or more embodiments of the containment, the inner packaging may include elements to hold the implantable medical device in place, such that the implantable medical device cannot move around inside the inner packaging when the inner packaging is closed. In at least one embodiment, the elements to hold the implantable medical device in place may, for example, be protruding contour elements of one or more walls of the inner packaging.

In one or more embodiments, the inner packaging may include elements to capacitively couple to an implantable medical device's communication electrode inside the inner packaging. As such, in at least one embodiment, the need for at least one inner feedthrough extending through the wall of the inner packaging is eliminated.

In at least one embodiment, the inner packaging may include a cavity that contains the medical device and the conductive medium for galvanic communications. In at least one embodiment, the inner packaging may include a tube or vial with at least one sealing cap. Thus, in one or more embodiments, the inner packaging may easily be opened without touching the implantable medical device or the conductive medium surrounding the implantable medical device. In at least one embodiment, such a configuration helps to keep the implantable medical device sterile.

In at least one embodiment, the inner packaging may include at least one protrusion to assist centering an implantable medical device within the inner packaging or to hold an implantable medical device within the inner packaging in place. In one or more embodiments, such a configuration helps to achieve consistent conditions for data communication with the implantable medical device.

In at least one embodiment, either some or all of the contacts or some or all of the outer feedthroughs or both may include spring contacts, such as pogo pins. Thus, in one or more embodiment, reliable contact between the electrically conducting elements is achieved.

In at least one embodiment, the sterilizable containment may include an implantable medical device within the inner packaging.

In one or more embodiments, the implantable medical device may include an implantable leadless pacemaker.

In at least one embodiment, the implantable medical device may allow impedance-based data communication with an external device.

According to one or more embodiments of the invention, a method of programming and/or testing an implantable medical device is provided. In at least one embodiment, the method may include the steps of:

placing the implantable medical device into a containment as disclosed herein, closing the containment containing the implantable medical device, sterilizing the containment containing the implantable medical device, and programming and/or testing the implantable medical device within the closed containment.

One or more embodiments of the invention provides a compact, ready-made device that communicates with an implantable medical device without requiring that such data exchange necessarily occurs after the implantable medical device is stationed within patient vasculature. At least one embodiment of the invention supports debug, test, activation, and programming capabilities without any need to remove the implant from sterile packaging. As such, by way of at least one embodiment, such capabilities may aid in adoption of leadless therapies, as clinicians may easily view the device in an operational state without needing to initiate a surgical procedure. From a quality assurance vantage, according to one or more embodiments, the manufacturer may additionally perform "up till the last possible minute" device evaluations, prior to sending the devices through the distribution channels.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 3:
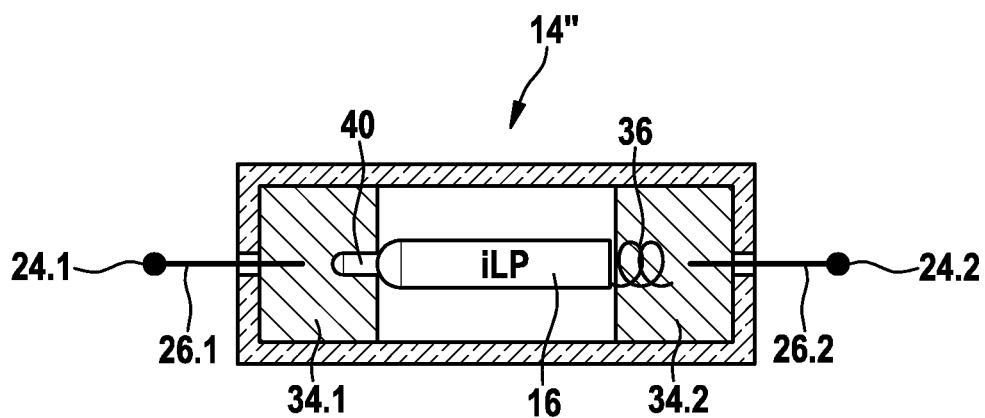
FIG. 3 illustrates an alternative inner packaging of a containment according to one or more embodiments of the invention.
Figure 4:
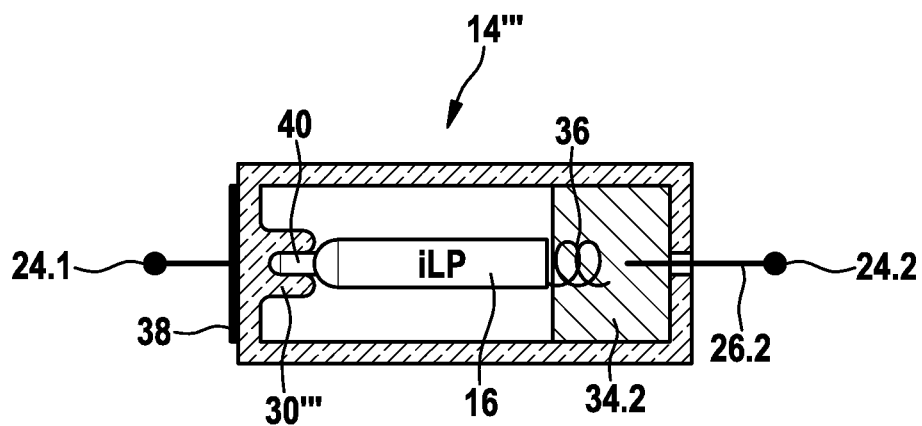
FIG. 4 discloses a further alternative inner packaging of a containment according to one or more embodiments the invention.

Four distinct embodiments of the invention are illustrated in detail. According to one or more embodiments, in FIG. 1 and FIG. 2, an inner packaging of the sterile containment surrounds the implantable medical device with a electrically conductive solution and electrical feedthroughs provide contacts to which the programmer may connect to transmit and receive data. At least one embodiment of the invention, as shown in FIG. 3, may include controlled electro-mechanical feedthroughs, native to the packaging, that offer a data conduit. One or more embodiments of the invention may include a built-in capacitive coupling hardware, again, native to the packaging, that enables dialogue between the implant and the programmer, as shown in FIG. 4.

Figure 1A:
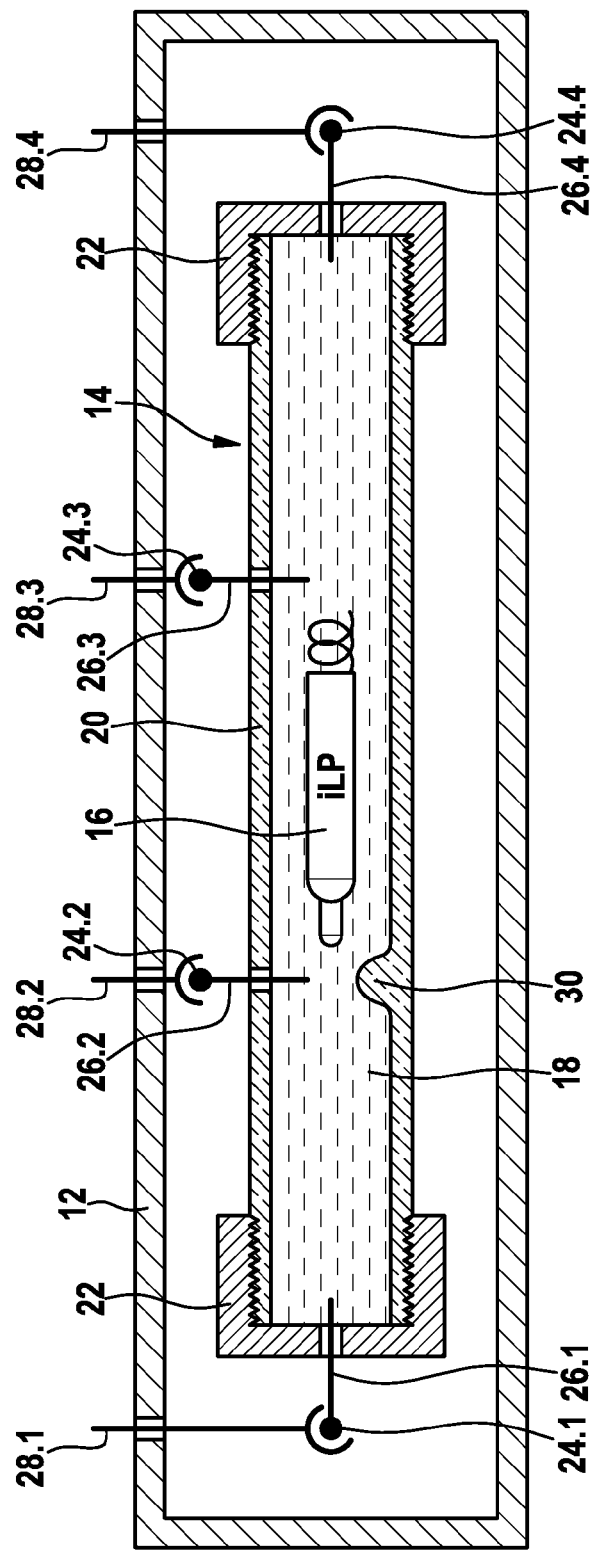
FIG. 1A illustrates a first embodiment of a containment, including an implantable medical device.

FIG. 1A illustrates a cross-sectional view of a containment 10 according to one or more embodiments of the invention. As shown in FIG. 1A, in at least one embodiment, the containment 10 includes an outer packaging 12 and an inner packaging 14. In one or more embodiments, the inner packaging 14 is enclosed by the outer packaging 12. By way of at least one embodiment, within the inner packaging 14, an implantable medical device 16 is included. In one or more embodiments, the implantable medical device 16 is an implantable leadless pacemaker (ILP) that may be programmed by way of galvanic or impedance-based communication.

To allow such galvanic or impedance-based communication, in at least one embodiment of the invention, the inner packaging 14 may include an electrically conductive medium 18, such as saline or a liquid conductive gel, in which the implantable medical device 16 is embedded.

As shown in FIG. 1A, according to at least one embodiment, the inner packaging 14 may include a tube 20 and two sealing caps 22 on both longitudinal ends of tube 20. In one or more embodiments, the 20 may be made from glass, or from polymers.

Figure 1B:
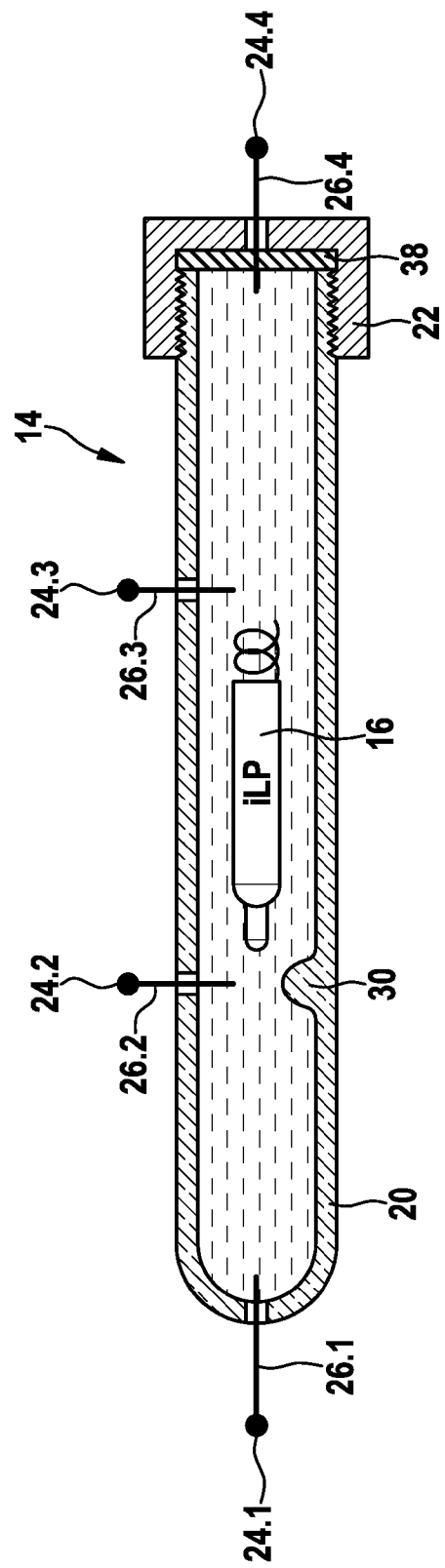
FIG. 1B illustrates an alternative embodiment of a containment, including an implantable medical device.

In at least one embodiment, the inner packaging 14 as shown in FIG. 1B may include a tubular body 20, wherein one of the longitudinal ends is closed and the other longitudinal end is closed with a sealing cap 22. In one or more embodiments, the sealing caps 22 may be screw-on caps and may include a gasket 38 to enable viable sealing.

By way of at least one embodiment, inner packing 14 may include at least two electric contacts, or four electric contacts 24.1, 24.2, 24.3 and 24.4 as shown in FIGS. 1A and 1B. In one or more embodiments, each electric contact, such as electric contacts 24.1, 24.2, 24.3 and 24.4 is part of a respective inner feedthrough 26.1, 26.2, 26.3 and 26.4, which penetrates tube 20 or cap 22, respectively, such that inner feedthroughs 26.1, 26.2, 26.3 and 26.4 each have electric contact to the medium 18 within inner packaging 14.

In at least one embodiment, outer packaging 12 may include four outer feedthroughs 28.1, 28.2, 28.3 and 28.4, each of which corresponds with one of the inner contacts 24.1, 24.2, 24.3 and 24.4. When both the inner packaging 14 and the outer packaging 12 are closed, in one or more embodiments, the outer feedthroughs 28.1, 28.2, 28.3 and 28.4 each have direct electric contact with a corresponding inner contact 24.1, 24.2, 24.3 and 24.4. According to at least one embodiment, to provide reliable electric contact in the closed state of the containment, either one of the two parts that contact each other may be a pogo pin or a similar spring contact. In at least one embodiment, the contacts may be made by pressing two conductive foil windows (one of the outer and inner package) together with a pattern of micro ridges. In one or more embodiments, the foil sheets may easily be separated when the outer package is opened.

In at least one embodiment, as shown in FIG. 1A, two of the outer feedthroughs and two of the inner contacts, such as feedthroughs 28.1 and 28.4 together with contacts 24.1 and 24.4, may be used to inject communication current or to impose a small electric field, while the other outer feedthroughs 28.2 and 28.3 together with the corresponding contacts 24.2 and 24.3 may be used as electrodes to measure a response from the implantable medical device 16. Thus, in one or more embodiments, when both the inner packaging 14 and the outer packaging 12 are closed and enclose the implantable medical device 16, a galvanic communication may occur, and even when the outer packaging is removed and only the inner packaging is still sealed, a communication may occur.

According to at least one embodiment of the invention, on the inside of tube 20, a protrusion or bump 30 may be provided that positions the implantable medical device 16 right in the center of tube 20. In one or more embodiments, in case the implantable medical device 16 has moved within the inner packaging 14, containment 10 may be tilted to reposition the implantable medical device 16 so it abuts bump 30.

By way of at least one embodiment, the containment may include only two outer feedthroughs and two contacts of the inner packaging. In at least one embodiment, injecting a current or imposing a small electric field and measuring the response from the implantable medical device 16 may occur over the same two inner and outer feedthroughs.

At least one embodiment of the invention, as shown in FIG. 1A, includes placement of the implantable medical device 16 (e.g. implantable leadless pacemaker) within a saline or conductive gel filled vial or tube 20. In one or more embodiments, the tube 20 may include bottle threads at one end or both ends. To cap the tube end(s), in at least one embodiment, one or two screw-on lids or sealing caps 22 each with an electrical feedthrough 26.1 and 26.4 may inject the communication current or may impose a small electric field. In one or more embodiments, two additional feedthroughs 26.2 and 26.3 may extend through either the end or the side of the tube 20 to provide connections 24.2 and 24.3 to measure response signals of the implantable medical device 16. In one or more embodiments, as shown in FIG. 1A and FIG. 1B, the inner packaging 14 (in particular tube 20) may include at least one "bump" feature 30 that allows the physician to tilt the tube 20 to one end and have the implantable medical device center itself between the feedthroughs 26.2 and 26.3. One or more embodiments may include multiple bumps to keep the medical device in the optimal location without tilting. This alignment, in at least one embodiment, optimizes the measurement of the response from the implantable medical device 16 and because the "bump" 30 is only on one side of the implantable medical device 16 simply unscrewing one cap 22 of the inner packaging allows the implantable medical device 16 to be removed from the inner packaging 14 without any need to break or cut into the saline-containing tube 20, and may avoid any need for special tools. One or more embodiments may include flexibility for removing the outer-most feedthroughs to further simplify the packaging design. In at least one embodiment, surrounding the inner packaging 14 is an outer packaging 12 that additionally provides electrical feedthroughs 28.1, 28.2, 28.3 and 28.4 that may support and/or enable communication. By way of one or more embodiments, using pogo-pin or similar design features may enable electrical connections from outside the outer packaging 12 all the way into the core of the inner packaging 14 where the implantable medical device 16 is located.

Figure 2:
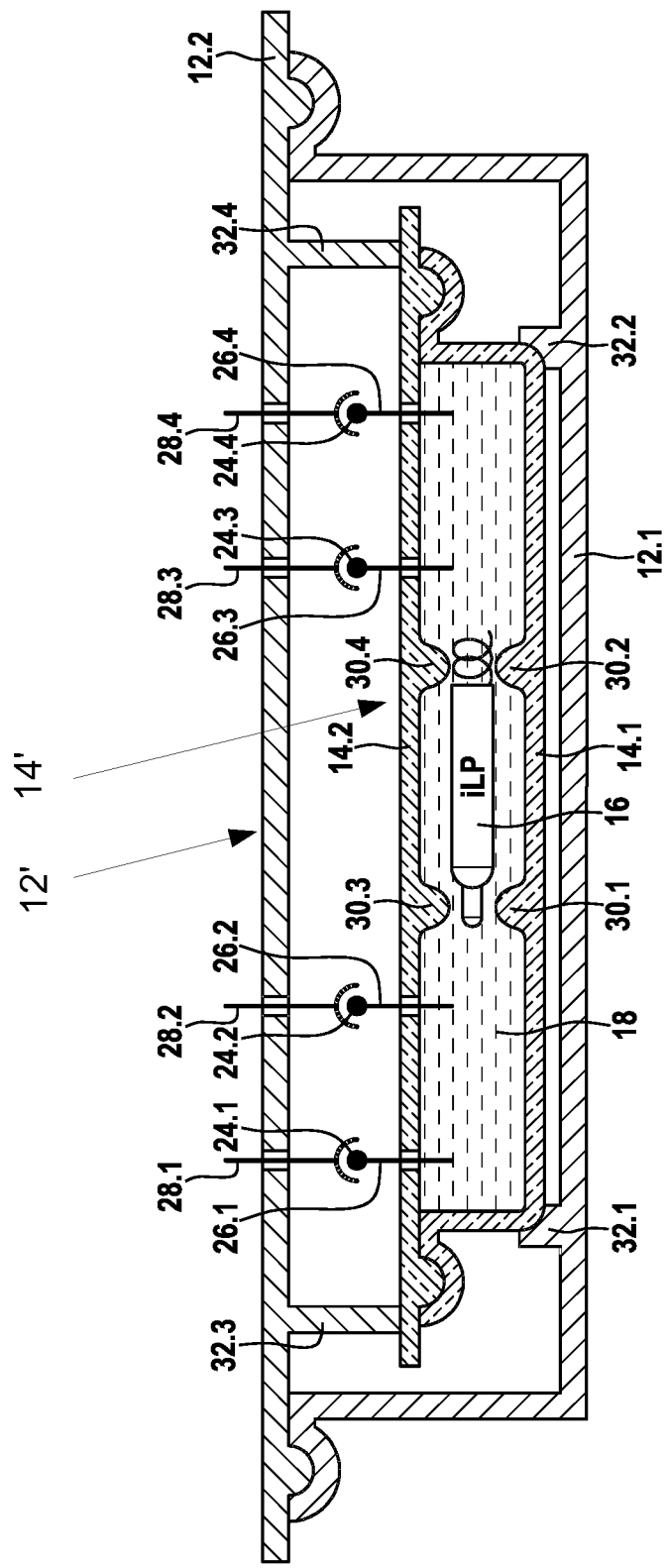
FIG. 2 illustrates an alternative embodiment of a containment, including an implantable medical device.

FIG. 2 illustrates an alternative embodiment of a containment, including an implantable medical device. According to at least one embodiment, FIG. 2 differs from FIG. 1 in that the inner packaging 14' and the outer packaging 12' are both designed as blister packages, each having a bottom part 12.1 and 14.1, respectively, and a lid part 12.2 and 14.2, respectively. In one or more embodiments, the lid parts 12.2 and 14.2 may be peeled off manually in order to open the outer packaging and the inner packaging, respectively.

As shown in FIG. 2, in at least one embodiment, outer feedthroughs 28.1, 28.2, 28.3 and 28.4 may extend through lid part 12.2 of outer packaging 12. In one or more embodiments, contacts 24.1, 24.2, 24.3 and 24.4 may be arranged on lid part 14.2 of inner packaging 14'. In at least one embodiment, inner packaging 14' may be filled with a liquid or semi-liquid electrically conducting medium, such as saline or electrically conducting gel. In at least one embodiment, similar to the containments shown in FIGS. 1A, 1B and 2, electrical feedthroughs 26.1, 26.2, 26.3 and 26.4 may pass through the inner packaging to enable data exchange. In one or more embodiments, the feedthroughs 26.1, 26.2, 26.3 and 26.4 may link to an additional set of outer feedthroughs 28.1, 28.2, 28.3 and 28.4 on an outer blister packaging 12'. As such, in at least one embodiment, communication is thus supported through all layers of the double sterile containment.

In one or more embodiments of the invention, bottom part 14.1 and lid part 14.2 of the inner packaging 14' may both include protrusions 30.1, 30.2, 30.3 and 30.4 extending into the interior of inner packaging 14' in order to hold the implantable medical device 16 in place. Similarly, in at least one embodiment, bottom part 12.1 and lid part 12.2 of outer packaging 12' may both include inwardly extending protrusions 32.1, 32.2, 32.3 and 32.4 in order to hold inner packaging 14' in place with outer packaging 12'. Thus, in one or more embodiments, the outer feedthroughs 28.1, 28.2, 28.3 and 28.4 will reliably contact contacts 24.1, 24.2, 24.3 and 24.4 of inner packaging 14'.

Again, by way of one or more embodiments, communication with the implantable medical device 16 may occur while keeping outer packaging and inner packaging closed, such that implantable medical device 16 is kept sterile.

Similar to the containments of FIGS. 1A and 1B, in at least one embodiment, communication with the implantable medical device 16 may occur when outer packaging 12' is opened but inner packaging 14' is still closed.

FIG. 3 shows a third illustration of an inner packaging 14", according to one or more embodiments of the invention. In at least one embodiment, inner packaging 14" may be placed within an outer packaging similar to FIGS. 1A, 1B and 2.

In at least one embodiment, in contrast to FIGS. 1A, 1B and 2, inner packaging 14" of FIG. 3 may not be filled with an electrically conducting liquid medium. Instead, in one or more embodiment, two parts 34.1 and 34.2 made from conductive solid material may be included inside inner packaging 14", and wherein the conductive solid material may contact communication electrodes of the implantable medical device 16 and may hold implant medical device 16 in place. In one or more embodiments, contacts 24.1 and 24.2 of inner packaging 14" together with inner feedthroughs 26.1 and 26.2 may establish an electric connection between contacts 24.1 and 24.2' and the two parts 34.1 and 34.2 of conductive solid material inside inner packaging 14".

Thus, at least one embodiment of the invention, as shown in FIG. 3, may include an electromechanical device that enables communication. In one or more embodiments, within the inner packaging 14", an anchor 36 acting as first communication electrode of the implantable medical device 16 may be inserted into the conductive solid material (such as a foam, a hydrogel, or a material akin to steel wool). In at least one embodiment, a separate piece or part of the conductive solid material may also be used to surround the second communication electrode 40 of the implantable medical device 16. In one or more embodiments, electrical feedthroughs 26.1 and 26.2 associated with the inner packaging 14" may then connect to the two independent parts 34.1 and 34.2 of conductive material to provide galvanic connection.

FIG. 4 illustrates an inner packaging 14'" that may be placed within an outer packaging, as disclosed in FIGS. 1A, 1B and 2, according to one or more embodiments of the invention. In at least one embodiment, inner packaging 14'" of FIG. 4 may include one part 34.2 of electrically conductive solid material inside inner packaging 14'" similar to the inner packaging shown in FIG. 3. As such, in one or more embodiments, direct electric connection between contact 24.2 and one of the communication electrodes of implantable medical device 16 is established.

According to at least one embodiment, to contact the other communication electrode 40 of implantable medical device 16, no feedthrough is provided as discussed above, but rather an electrode 38 (coupling plate) connected to contact 24.1 is provided for capacitively coupling to the corresponding communication electrode of the implantable medical device 16.

In one or more embodiments, inner packaging 14'" may include an inwardly extending protrusion 30'" to hold the implantable medical device 16 in place.

As shown in FIG. 4, at least one embodiment may reduce the need for inner feedthroughs to a single feedthrough 26.1. By way of one or more embodiment, such a configuration may lead to a package design simplification, which provides both, easy manufacturing and reliable sealing of the packaging of the containment.

In at least one embodiment of the invention, the electrical interfacing with the implantable medical device's second communication electrode 40 may be supported via capacitive coupling. In one or more embodiments, such a strategy may eliminate one of the inner packaging feedthroughs and simplifies the overall packaging design. At least one embodiment of the invention may couple to the electrode 40 from outside of the outer packaging, eliminating the need to station a coupling plate 38 on the inner packaging 14'''.

One or more embodiments of the invention may use capacitive coupling rather than a feedthrough to pass the signal through the hermetic package. Once inside the package, in at least one embodiment, electrical contacts may then carry the signal to the device electrodes. Such a configuration differs from FIG. 4, where the capacitive couple is directly to the implant rather than to metal inside the package, which contact the electrode.

Figure 5:
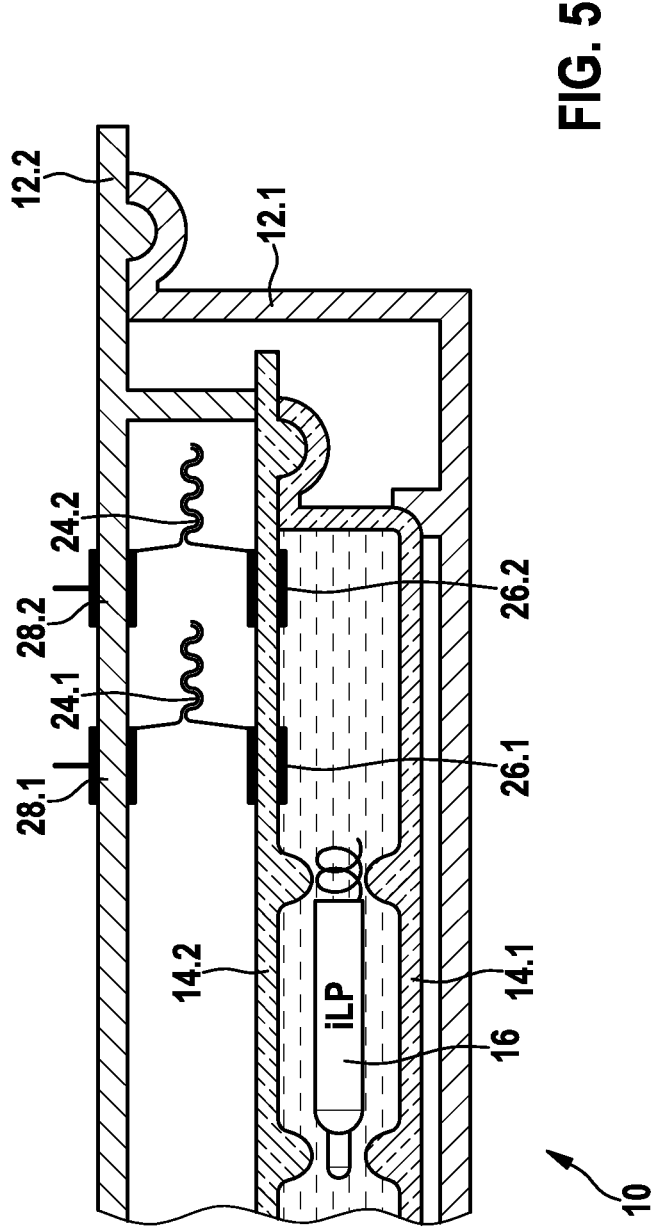
FIG. 5 discloses an alternative embodiment of the containment shown in FIG. 2.

In at least one embodiment, similar to the containment of FIG. 2, inner and outer feedthroughs may include capacitors. In at least one embodiment as shown in FIG. 5, the outer packaging 12 and the inner packaging 14, as also shown in FIG. 2, may both include blister packages, each having a bottom part 12.1 and 14.1, respectively, and a lid part 12.2 and 14.2, respectively. In one or more embodiments, the lid parts 12.2 and 14.2 may be peeled off manually in order to open the outer packaging and the inner packaging, respectively. In FIG. 5, only the right part of the containment is shown.

Figure 6:
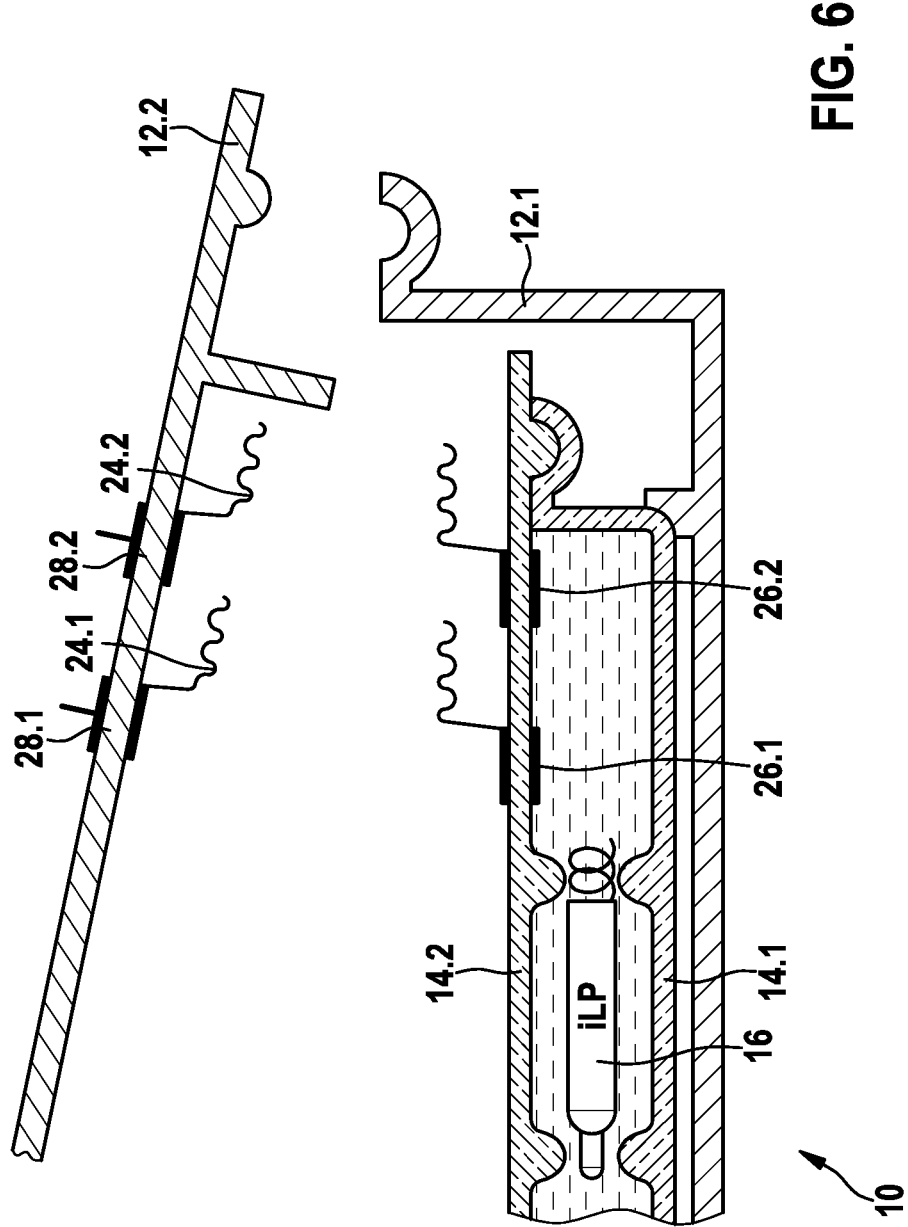
FIG. 6 discloses the containment shown in FIG. 5, with the outer packaging opened.

As shown in FIG. 5, in one or more embodiments, outer feedthroughs 28.1 and 28.2 and inner feedthroughs 26.1, 26.2 may be arranged as capacitive couplings through lid part 12.2 of outer packaging 12 and through lid part 14.2 of inner packaging 14 respectively. To enable capacitive coupling, according to at least one embodiment, inner and outer feedthroughs may include metallic foil pads arranged at the outer and inner side of inner and outer lid part 12.2 and 14.2 respectively. In one or more embodiments, two opposite metallic foil pads and the dielectric material of lid parts may form a capacitor. In at least one embodiment, the capacitors of the outer and inner packaging form the feedthroughs and may be connected by contacts 24.1 and 24.2. In one or more embodiments, contacts 24.1 and 24.2 may be made by pressing two conductive foil windows (one of the outer and inner package) together with a pattern of micro ridges. In at least one embodiment, the foil sheets may easily be separated when the outer package is opened as shown in FIG. 6. In one or more embodiments, inner packaging 14' may be filled with a liquid or semi-liquid electrically conducting medium, such as saline or electrically conducting gel. As such, in at least one embodiment, communication is thus supported through all layers of the double sterile containment.

In at least one embodiment, communication, in particular using small electric fields, with the implantable medical device 16 may occur while keeping outer packaging and inner packaging closed, such that implantable medical device 16 is kept sterile.

FIG. 6 discloses the containment shown in FIG. 5, with the outer packaging opened, according to one or more embodiments of the invention. Similar to the containments of FIG. 1A and FIG. 1B, in at least one embodiment of the invention, communication with the implantable medical device 16 may occur when outer packaging is opened but inner packaging is still closed.

In at least one embodiment, feedthroughs for galvanic communication may be included through the inner package, but not the outer package. Rather, in one or more embodiments, long sterilizable wires may be included inside the outer package which connect to the feedthroughs of the inner package. In at least one embodiment, when a user want to communicate with the device prior to implant, the user may open the outer package, and then may run the sterile wire to a device programmer outside of the sterile field. In one or more embodiments, the wands are inside of the sterile field during implants, but cables may run from the wand to a medical device programmer outside of the sterile field. As such, in at least one embodiment of the invention, less feedthroughs are required.

According to one or more embodiments, after packaging the implantable medical device in double containment, the entire assembly may proceed through a sterilization process. In one or more embodiments of the invention, the packaging may employ either gamma irradiation and/or ultra-violet exposure techniques.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS 10 containment
12, 12' outer packaging or outer blister packaging
14, 14', 14'', 14''' inner packaging
16 medical device
18 conductive medium
20 tube
22 caps
24.1, 24.2, 24.3, 24.4. electric contact
26.1, 26.2, 26.3, 26.4. inner feedthrough
28.1, 28.2, 28.3, 28.4 outer feedthrough
30 bump
30.1, 30.2, 30.3, 30.4 protrusion
32.1, 32.2, 32.3, 32.4 extending protrusion
34.1, 34.2 parts made from conductive solid material
36 anchor
38 gasket
40 electrode

What is claimed is:

1. A sterilizable containment for an implantable medical device comprising:
an inner packaging; and,
an outer packaging that encloses said inner packaging;
wherein said outer packaging comprises at least two electric feedthroughs and,
wherein said inner packaging comprises
at least two electric contacts,
wherein each of the contact at least two electric contacts of the inner packaging match one of the feedthroughs of the outer packaging to provide an electric connection between a respective feedthrough and the corresponding contact when the inner packaging and the outer packaging are closed,
wherein each of the at least two electric contacts feed one or more of electrical charge and voltage drops from outside the inner packaging to inside of the inner package and vice versa; and, an electrically conducting medium that allows one or more of propagation of electrical charge and application of a voltage delta between said at least two electric contacts of the inner packaging and an implantable medical device contained in said inner packaging.

2. The sterilizable containment according to claim 1, wherein the electrically conducting medium is a fluid.

3. The sterilizable containment according to claim 1, wherein the outer packaging further comprises four feedthroughs and the inner packaging further comprises four contacts.

4. The sterilizable containment according to claim 1, wherein the four contacts of the inner packaging part of four inner feedthroughs that feed one or more of electrical charge and voltage differences from the outside of said inner packaging to the electrically conducting medium inside the inner packaging.

5. The sterilizable containment according to claim 1, wherein said at least two electric feedthroughs are capacitors.

6. The sterilizable containment according to claim 1, wherein the inner packaging further comprises a coupling device that capacitive coupes to a communication electrode of said implantable medical device inside the inner packaging.

7. The sterilizable containment according to claim 1, wherein the inner packaging further comprises a tube or vial with at least one sealing cap.

8. The sterilizable containment according to claim 1, wherein the inner packaging further comprises at least one protrusion to assist centering said implantable medical device within the inner packaging or to hold said implantable medical device within the inner packaging.

9. The sterilizable containment according to claim 1, wherein alone or more of the at least two electric contacts or one or more of the at least two electric feedthroughs or both one or more of the at least two electric contacts and one or more of the at least two electric feedthroughs include spring contacts.

10. The sterilizable containment according to claim 1, further comprising an implantable medical device within the inner packaging.

11. The sterilizable containment according to claim 10, wherein the implantable medical device is an implantable leadless pacemaker.

12. The sterilizable containment according to claim 10, wherein the implantable medical device communicates with an external device using galvanic or electric field based data communication.

13. The sterilizable containment according to claim 10, wherein the implantable medical device is stored in shelf mode and is activated to an active mode prior to implantation.

14. The sterilizable containment according to claim 1, wherein said containment with said implantable medical device is configured to be closed and sterilized, and wherein the implantable medical device within the containment that is closed is configured to be one or more of programmed and tested.

15. A method of communicating with an implantable medical device, said method comprising:
placing the implantable medical device into a containment,
wherein said containment comprises
an inner packaging; and,
an outer packaging that encloses said inner packaging;
wherein said outer packaging comprises at least two electric feedthroughs and,
wherein said inner packaging comprises
at least two electric contacts,
wherein each of the at least two electric contacts of the inner packaging match one of the at least two electric feedthroughs of the outer packaging to provide an electric connection between a respective feedthrough and the corresponding contact when the inner packaging and the outer packaging are closed,
wherein each of the at least two electric contacts feed one or more of electrical charge and voltage drops from outside the inner packaging to inside of the inner package and vice versa; and,
an electrically conducting medium that allows one or more of propagation of electrical charge and application of a voltage delta between said at least two electric contacts of the inner package and an implantable medical device in said inner packaging;
closing the containment that includes the implantable medical device,
sterilizing the containment that includes the implantable medical device; and,
one or more of programming and testing the implantable medical device within the containment that is closed.

* * * * *